US010813646B2

(12) United States Patent
Li

(10) Patent No.: US 10,813,646 B2
(45) Date of Patent: Oct. 27, 2020

(54) LEFT ATRIAL APPENDAGE OCCLUDER

(71) Applicant: LIFETECH SCIENTIFIC (SHENZHEN) CO., LTD, Shenzhen (CN)

(72) Inventor: Anning Li, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 235 days.

(21) Appl. No.: 15/763,203

(22) PCT Filed: Aug. 1, 2016

(86) PCT No.: PCT/CN2016/092753
§ 371 (c)(1),
(2) Date: Mar. 26, 2018

(87) PCT Pub. No.: WO2017/071353
PCT Pub. Date: May 4, 2017

(65) Prior Publication Data
US 2018/0271538 A1 Sep. 27, 2018

(30) Foreign Application Priority Data

Oct. 28, 2015 (CN) .......................... 2015 1 0714210

(51) Int. Cl.
*A61B 17/12* (2006.01)
*A61B 17/00* (2006.01)
(52) U.S. Cl.
CPC ........ *A61B 17/12122* (2013.01); *A61B 17/12* (2013.01); *A61B 17/12031* (2013.01);
(Continued)
(58) Field of Classification Search
CPC ........ A61B 17/12031; A61B 17/12122; A61B 17/12172
See application file for complete search history.

(56) References Cited

U.S. PATENT DOCUMENTS 5,725,552 A * 3/1998 Kotula ............... A61B 17/0057
604/285
6,652,555 B1 * 11/2003 VanTassel .......... A61B 17/0057
128/898
(Continued)

FOREIGN PATENT DOCUMENTS

CN 101304693 A 11/2008
CN 103598902 A 2/2014
(Continued)

OTHER PUBLICATIONS

International Search Report with Written Opinion dated Nov. 2, 2016 of corresponding International application No. PCT/CN2016/092753; 13 pgs.

*Primary Examiner* — Gregory A Anderson
(74) *Attorney, Agent, or Firm* — Maier & Maier, PLLC

(57) ABSTRACT

A left atrial appendage occluder includes a sealing plate, a fixing plate, and a connection member connecting the sealing plate and the fixing plate. The connection member is a silk woven structure. A radial deformability of the sealing plate is greater than a radial deformability of the fixing plate, and/or an axial deformability of the sealing plate is greater than an axial deformability of the fixing plate. In the left atrial appendage occluder, the fixing plate and the sealing plate are connected via the connection member of the silk woven structure, such that a distance between the fixing plate and the sealing plate and an angle formed thereby are both adjustable to adapt to a left atrial appendage having a large bending angle or requiring the fixing plate to remain at an increased distance to the sealing plate, thereby reducing the risk of failed occlusion.

13 Claims, 10 Drawing Sheets

(52) U.S. Cl.
CPC ............... *A61B 17/12172* (2013.01); *A61B 2017/00477* (2013.01); *A61B 2017/00862* (2013.01); *A61B 2017/00867* (2013.01)

(56) References Cited

U.S. PATENT DOCUMENTS

| | | | |
|---|---|---|---|
| 8,828,051 B2 * | 9/2014 | Javois .............. | A61B 17/12172 606/213 |
| 2007/0265656 A1 * | 11/2007 | Amplatz ............ | A61B 17/0057 606/200 |
| 2008/0200945 A1 * | 8/2008 | Amplatz .......... | A61B 17/12172 606/195 |
| 2013/0218193 A1 | 8/2013 | Erzberger et al. | |

FOREIGN PATENT DOCUMENTS

| | | |
|---|---|---|
| CN | 103705274 A | 4/2014 |
| CN | 103889339 A | 6/2014 |
| CN | 203634235 U | 6/2014 |
| CN | 204181678 U | 3/2015 |

\* cited by examiner

LEFT ATRIAL APPENDAGE OCCLUDER

FIELD

The present application relates to a medical device, and more particularly relates to a left atrial appendage occluder.

BACKGROUND

At the present, an occluder may be put into a left atrial appendage through a catheter intervention method to prevent a left atrial appendage thrombus caused by atrial fibrillation and avoid apoplexy caused by a fact that the thrombus goes up to a brain, or prevent systematic embolization caused by a fact that the thrombus reaches other portions of a body through a blood circulation system of a human body. Such left atrial appendage occluders substantially include an integrated occluder and a split type occluder according to its structure. For example, the split type occluder generally includes a fixing component and a sealing component which are connected with each other; the fixing component is disposed in a cavity of the left atrial appendage to fix the whole occluder; and the sealing component seals an opening portion of the left atrial appendage to block flowing of blood flow into the cavity of the left atrial appendage.

For the split type occluder of this type, a connection restriction is set between its fixing component and sealing component, which means that one component would be pulled by the other component, and the two components may not deform independently completely. For example, after being fixed in the cavity of the left atrial appendage, the fixing component would pull the sealing component during adaption to the cavity structure of the left atrial appendage and in the activity process of the left atrial appendage; during pulling, a phenomenon that the sealing component cannot be fully fitted to the opening portion of the left atrial appendage is possibly caused, and a blood flow leaking channel would be formed between a left atrium and the left atrial appendage, so that an optimal sealing effect may not be achieved, and afterwards, the thrombus in the left atrial appendage flows out of the left atrial appendage, which leads to the apoplexy.

SUMMARY

In view of the above-mentioned problems, it is necessary to provide a left atrial appendage occluder with a good sealing effect and a high adaptability.

A technical scheme adopted to solve the technical problems is as follows: a left atrial appendage occluder is provided, including a sealing plate, a fixing plate located on one side of the sealing plate, and a connection member for connecting the sealing plate with the fixing plate, and the connection member is of a filament woven structure.

A radial deformability of the sealing plate is greater than that of the fixing plate and/or an axial deformability of the sealing plate is greater than that of the fixing plate.

According to the left atrial appendage occluder provided by the embodiment of the present application, under the action of same radial force, a radial length variation of the sealing plate is more than that of the fixing plate; or under the action of the same radial force, a radial length change rate of the sealing plate is more than that of the fixing plate; or under the action of same axial force, a displacement of the sealing plate along the axial force direction is more than that of the fixing plate along the axial force direction.

According to the left atrial appendage occluder provided by the embodiment of the present application, the connection member is of an elastic filament woven structure.

According to the left atrial appendage occluder provided by the embodiment of the present application, the connection member is of a disk shape or a barrel shape in a naturally unfolded state.

According to the left atrial appendage occluder provided by the embodiment of the present application, the peripheral surface of the connection member has an annular recess.

According to the left atrial appendage occluder provided by the embodiment of the present application, a recess is formed near a joint on at least one of end surfaces of the connection member connected with the sealing plate and connected with the fixing plate.

According to the left atrial appendage occluder provided by the embodiment of the present application, in the naturally unfolded state, the maximum radial length of the connection member is shorter than that of the fixing plate.

According to the left atrial appendage occluder provided by the embodiment of the present application, in the naturally unfolded state, at least one portion of the connection member extends out of a space encircled by the fixing plate.

According to the left atrial appendage occluder provided by the embodiment of the present application, the connection member includes a first fixed connection member, a second fixed connection member and a woven body formed by weaving filaments; the first end of the woven body is collected and fixed by the first fixed connection member; and the second end of the woven body is collected and fixed through the second fixed connection member.

According to the left atrial appendage occluder provided by the embodiment of the present application, the sealing plate is of a filament woven structure; one end of the sealing plate is connected with one side of the connection member; the fixing plate includes a plurality of supporting members; one end of each supporting member radiates and extends from the other side of the connection member; and the multiple supporting members cooperatively form an umbrella-shaped structure.

In the left atrial appendage occluder of the present application, the fixing plate and the sealing plate are connected through the connection member of the filament woven structure, so that a distance between the fixing plate and the sealing plate and an angle formed thereby are both adjustable to adapt to a left atrial appendage having a large bending angle (such as a chicken-wing shape) or requiring the fixing plate to remain at an increased distance to the sealing plate (such as a conical shape), thereby reducing a risk of failed occlusion of the left atrial appendage. In addition, as the distance between the fixing plate and the sealing plate is adjustable, the fixing plate may be located at a deep portion of the left atrial appendage to improve the fixing stability of the occluder and reduce a risk of device embolization.

In addition, the filament woven structure featuring elastic extension and retraction may achieve a buffer effect on an interaction force between the fixing plate and the sealing plate, thereby lowering the probability of poor fitting of the sealing plate to an opening portion of the left atrial appendage and reducing long-term leakage; and injury caused by puncture of a cavity wall of the left atrial appendage by the fixing plate may be lowered by alleviating stress on the fixing plate, thereby reducing a risk of hydropericardium.

In addition, the sealing plate is configured to have a larger deformation amount or deformation rate than the fixing plate. Therefore, in a pulling process, the sealing plate deforms more easily to better get close to and be better fitted to the opening portion of the left atrial appendage. Moreover, as the elastic and flexible connection member is arranged, a sealing effect of the sealing plate may be further improved. In addition, as the sealing plate deforms more easily, wear to a tissue at the opening portion of the left atrial appendage may be further correspondingly reduced, and the possibility of occurrence of inflammation, hydropericardium and even pericardial tamponade may be also reduced.

DETAILED DESCRIPTION OF THE DRAWINGS

For the purpose of making the description of a structure of a left atrial appendage occluder clearer, the present application defines terms "distal end" and "proximal end". The above-mentioned terms are commonly used terms in the field of interventional medical devices. To be more specific, the "distal end" represents an end far away from an operator in a surgical process, and the "proximal end" represents an end close to the operator in the surgical process.

Figure 1:
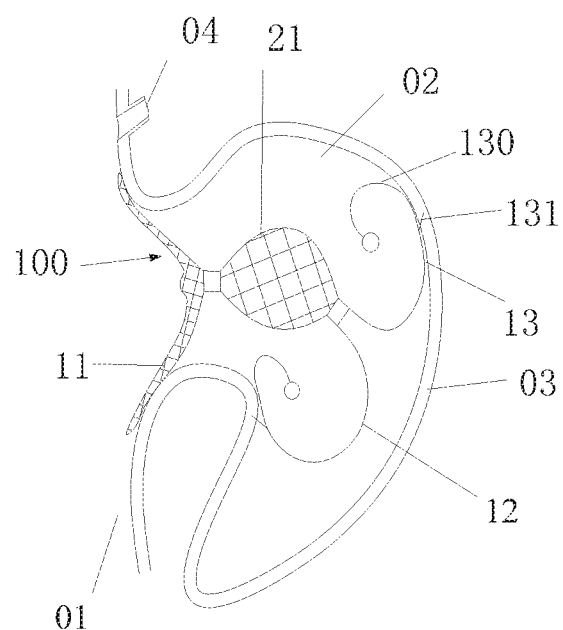
FIG. 1 is a schematic diagram of a state that a left atrial appendage occluder provided by one embodiment of the present application is implanted into a chicken-wing-shaped left atrial appendage.
Figure 2:
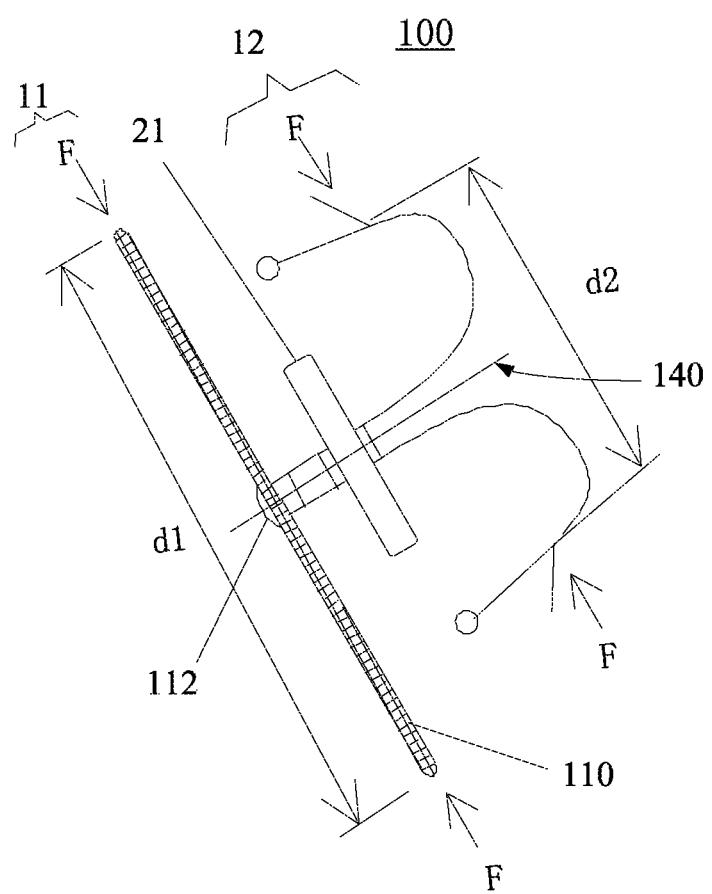
FIG. 2 is a schematic diagram of a structure of a left atrial appendage occluder provided by one embodiment of the present application.

FIG. 1 is a schematic diagram of a state that a left atrial appendage occluder 100 according to one embodiment of the present application is implanted into a left atrial appendage. The left atrial appendage 02 is located between a bicuspid valve (not shown in the figure) and a left superior pulmonary vein 04 in a left atrium 01. The left atrial appendage occluder includes a sealing plate 11, a fixing plate 12 located on one side of the sealing plate 11 and a connection member 21 for connecting the sealing plate 11 with the fixing plate 12; and the connection member 21 is of a filament woven structure. For example, the filament woven structure may be an elastic filament woven structure. On one hand, setting of a weaving mode makes the filament woven structure elastic, and on the other hand, adoption of an elastic filament (such as a nickel-titanium metal wire) makes the filament woven structure elastic.

The connection member 21, which is disposed between the fixing plate 12 and the sealing plate 11 and is of the filament woven structure, has a relatively high bending flexibility; under the action of the fixing plate 12 and the sealing plate 11, the connection member 21 may elastically extend and retract or bend to compensate an included angle and a distance between the fixing plate 12 and the sealing plate 11; therefore, when a cavity of the left atrial appendage 02 has a relatively large bending angle, for example, when the cavity of the left atrial appendage 02 is of a chicken wing shape as shown in FIG. 1, the connection member 21 may adapt to the shape of the cavity of the left atrial appendage only through its extension and retraction and/or bending instead of remaining coaxiality of the fixing plate 12 and the sealing plate 11, thereby stably fixing the left atrial appendage occluder 100 in the left atrial appendage and preventing it from falling. In addition, after the left atrial appendage occluder 100 is implanted, and when the fixing plate 12 and the sealing plate 11 pull each other, the connection member 21 capable of elastically extending and retracting or bending may achieve a buffer effect on the pulling force, thereby lowering injury from the puncture of a cavity wall of the left atrial appendage by the fixing plate via alleviating stress on the fixing plate to reduce a risk of hydropericardium, and reducing a displacement of the sealing plate 11 at the same time to guarantee an optimal fitting sealability between the sealing plate 11 and an opening portion of the left atrial appendage.

For example, the sealing plate 11 is of a filament woven structure formed by multiple weaving filaments which may be made of a shape memory material (such as a nickel-titanium alloy); one end of the sealing plate 11 is adjacent to the connection member 21, for example, the end of the sealing plate 11 and the connection member may be fixedly connected to each other in a welding or riveting way; the other end of the sealing plate 11 is detachably connected with a deliverer in a delivery process of the left atrial appendage occluder 100, and the detachable connection may be threaded connection. For example, with reference to FIG. 6, the weaving filaments on the end surface 110 of the sealing plate 11 are gathered and fixedly accommodated at an end socket 112; and the end socket 112 is detachably connected with the deliverer.

The fixing plate 12 includes multiple supporting members 13; one end of each supporting member 13 is connected with the connection member 21, and may be fixedly connected with the connection member 21 in a welding or riveting manner; the other end of each supporting member 13 radiates and extends from the other side of the connection member; the multiple supporting members 13 cooperatively form an umbrella-shaped structure; and each supporting member 13 includes a suspended supporting section 130. The fixing plate 12 may be manufactured by using a cutting mode. For example, the fixing plate 12 may be integrally cut from a metal tube; the metal tube may be made of a shape memory material, such as the nickel-titanium alloy. In some embodiments, anchor burrs 131 may be further formed on the suspended supporting sections 130; and the anchor burrs 131 are inserted into a cavity wall 03 of the left atrial appendage 02 to fixedly connect the fixing plate with the cavity wall 03. When the left atrial appendage occluder 100 implanted into a human body is released and unfolded, the fixing plate 12 is put into a cavity of the left atrial appendage 02 and is fixedly fitted with the cavity wall 03 of the left atrial appendage 02; and the sealing plate 11 covers an opening of the left atrial appendage 02.

Figure 6:
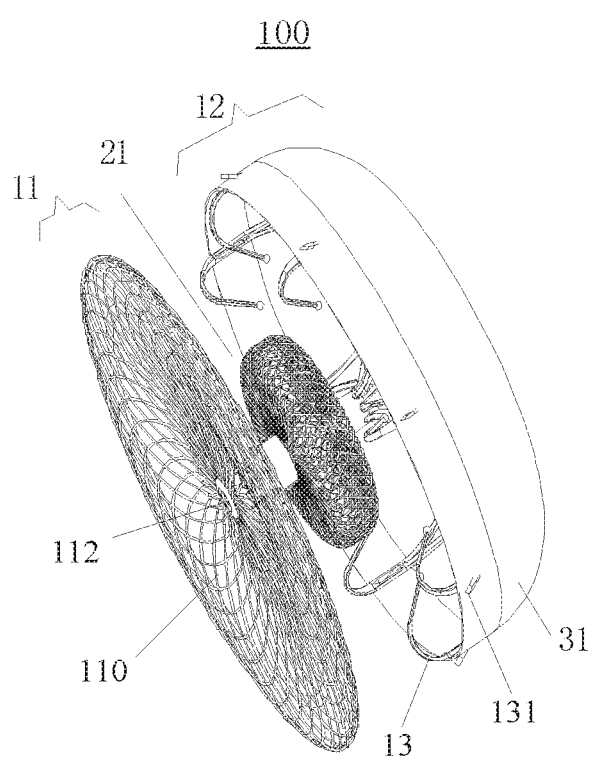
FIG. 6 is a schematic diagram of another structure of a left atrial appendage occluder provided by one embodiment of the present application.

Further, with reference to FIG. 6, the fixing plate 12 further includes film bodies 31 disposed on the supporting members 13. The film bodies 31 are generally made of a PET (polyethylene terephthalate) or PTFE (polytetrafluoroethylene) or silica gel material, or other film materials having satisfactory biocompatibility and physical property. The film bodies 31 are fixed on the supporting members 13 of the fixing plate 12 through the anchor burrs 131 in a suturing way. When the left atrial appendage occluder 100 is implanted into the left atrial appendage, the anchor burrs 131 are inserted into the cavity wall of the left atrial appendage, and the film bodies 31 form an outer surface, which is in contact with the cavity wall of the left atrial appendage, of the fixing plate 12.

Figure 3:
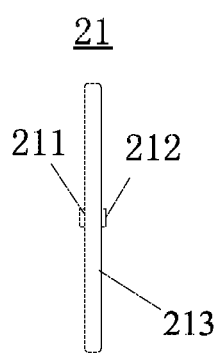
FIG. 3 is a schematic diagram of an actual working state of a connection device connected between a fixing plate and a sealing plate in one embodiment of the present application, showing a state of the connection device without stress.

With reference to FIG. 3, the connection member 21 includes a first fixed connection member 211, a second fixed connection member 212 and a woven body 213 formed by weaving filaments. The first end of the woven body 213 is collected and fixed by the first fixed connection member 211; and the second end of the woven body 213 is collected and fixed through the second fixed connection member 212. The first fixed connection member 211 is connected with the sealing plate 11, and the second fixed connection member 212 is connected with the fixing plate 12, thereby connecting the sealing plate 11 with the fixing plate 12 through the connection member 21.

Figure 4:
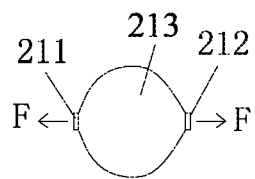
FIG. 4 is a schematic diagram of an actual working state of a connection device connected between a fixing plate and a sealing plate in one embodiment of the present application, showing a state under a first stress.
Figure 5:
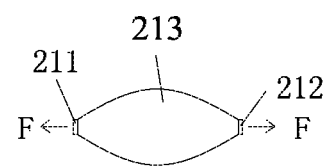
FIG. 5 is a schematic diagram of an actual working state of a connection device connected between a fixing plate and a sealing plate in one embodiment of the present application, showing a state under a second stress.

The woven body 213 woven by the filaments may elastically extend and retract or bend under the action of an external force. For example, FIG. 3 shows the connection member 21 in a naturally unfolded state, and FIG. 4 and FIG. 5 respectively show a condition that the woven body 213 in FIG. 3 is pulled to deform under the external force, wherein the woven body 213 as shown in FIG. 3 is flat without the external force; the woven body 213 in FIG. 4 retracts in a radial direction and extends in an axial direction after being pulled by a force F, so that a relative distance between the first fixed connection member 211 and the second fixed connection member 212 is increased; with further pulling of the force F, the woven body 213 in FIG. 5 further retracts in the radial direction and extends in the axial direction, so that the relative distance between the first fixed connection member 211 and the second fixed connection member 212 is further increased. FIGS. 3 to 5 only show the elastic extension and retraction conditions of the woven body 213 woven by the filaments under the action of the external force, but a person skilled in the art should understand that under the action of the external force, the woven body 213 woven by the filaments still may elastically bend, and no details are given here.

It can be seen from the above-mentioned description that under the action of the external force, such as the pulling action of the sealing plate 11 and/or the fixing plate 12, the connection member 21 may change a distance between the first fixed connection member 211 and the second fixed connection member 212, and may further change an angle between the first fixed connection member 211 and the second fixed connection member 212, thereby correspondingly and adaptively adjusting a length and/or an angle between the sealing plate 11 and the fixing plate 12. Therefore, the left atrial appendage occluder 100 provided by the present application may meet implantation requirements of the left atrial appendages 02 of different shapes such as the chicken-wing shape and a conical shape. In addition, under the pulling action of the sealing plate 11 and/or the fixing plate 12, with the filament woven structure, the connection member 21 may buffer the influence of the pulling force on the sealing plate 11 and the fixing plate 12 by right of its high elastic extension, retraction and bending performance.

The woven body 213 is formed by weaving 1 to 168 metal wires, preferably 12 to 144 metal wires, such as the nickel-titanium metal wires, and the diameter of each metal wire is 0.01 to 0.5 mm. The diameters and the number of the metal wires may be reasonably matched, and the metal wires are sized through thermal treatment. Further, the surfaces of the metal wires may be coated with bioceramic films, so that the flexible connection member 21 has proper hardness while keeping certain elasticity.

Figure 7:
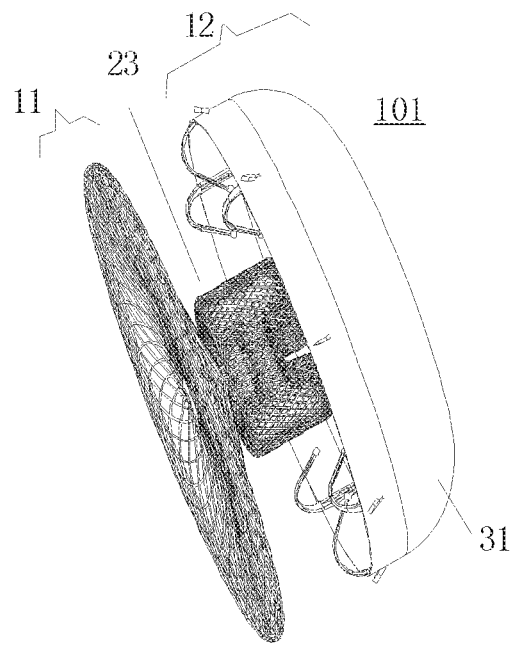
FIG. 7 is a schematic diagram of a structure of a left atrial appendage occluder provided by another embodiment of the present application.
Figure 8:
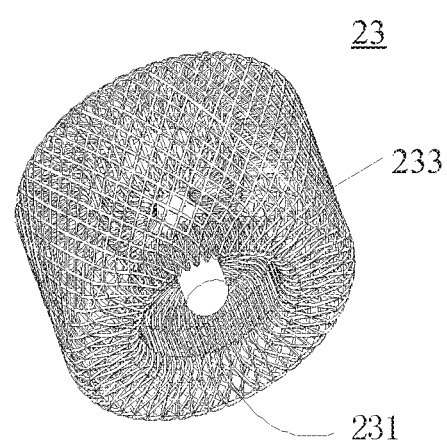
FIG. 8 is a schematic diagram of a structure of a connection member connected between a fixing plate and a sealing plate in FIG. 7.

With reference to FIG. 6, according to one specific implementation embodiment of the present application, in the naturally unfolded state of the left atrial appendage occluder 100, the connection member 21 is of a disk shape. The so-called disk shape is that the radial length of the woven body 213 is obviously longer than the axial length. Or with reference to FIG. 7 and FIG. 8, in the naturally unfolded state of the left atrial appendage occluder 100, the connection member 23 is of a barrel shape. The so-called barrel shape is that the radial length of the filament woven structure is equal to the axial length, the radial length is slightly longer than the axial length, or the radial length is shorter than the axial length. A recess 231 is defined near a joint on at least one of end surfaces of the connection member 23 connected with the sealing plate 11 and connected with the fixing plate 12. By formation of the recess 231 on the end surface of the woven body 233 woven by the filaments, the woven body 233 may have a larger extension and retraction degree and bending amplitude to adapt to longer distance and angle adjustment between the sealing plate 11 and the fixing plate 12 in a wider range.

Figure 9:
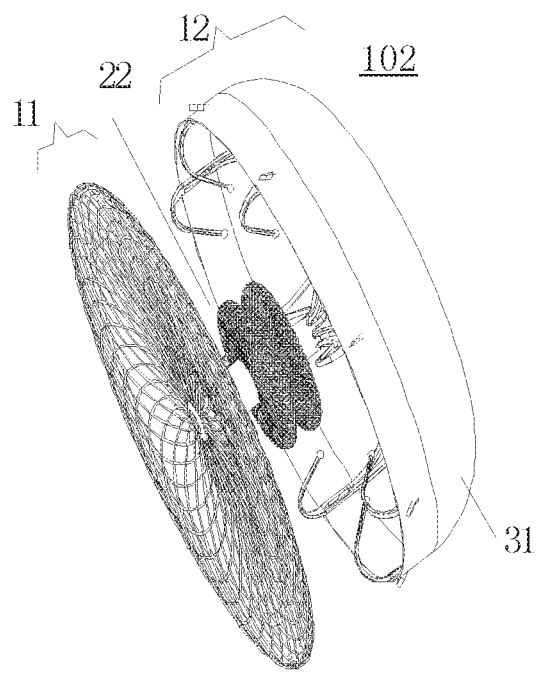
FIG. 9 is a schematic diagram of a structure of a left atrial appendage occluder provided by another embodiment of the present application.
Figure 10:
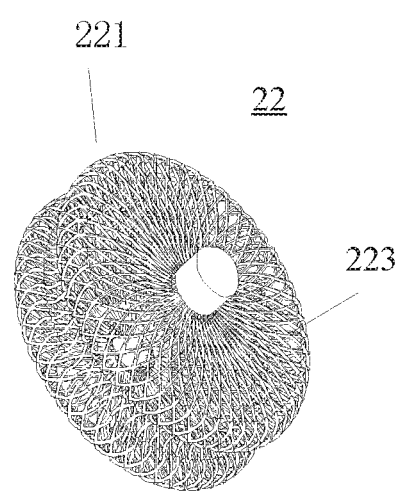
FIG. 10 is a schematic diagram of a structure of a connection member connected between a fixing plate and a sealing plate in FIG. 9.

With reference to FIG. 9 and FIG. 10, according to another specific implementation embodiment of the present application, in the naturally unfolded state of the left atrial appendage occluder 102, the peripheral surface of the woven body 223 of the connection member 22 has an annular recess 221. By formation of the recess 221 on the peripheral surface of the woven body 223 by the filaments, the woven body 223 may have a larger extension and retraction degree and bending amplitude to adapt to longer distance and angle adjustment between the sealing plate 11 and the fixing plate 12 in a wider range.

With reference to FIGS. 1 to 10, in the naturally unfolded state of the left atrial appendage occluder, at least one portion of its connection member may extend out of a space encircled by the fixing plate; at the moment, the remaining portion of the connection member may be located in the space encircled by the fixing plate. Therefore, one portion of the connection member extending into the space encircled by the fixing plate may shorten the distance (which may be called a waist length) between the fixing plate and the sealing plate, and one portion of the connection member extending out of the space encircled by the fixing plate may avoid mutual influence caused by an extremely short distance between the fixing plate and the sealing plate, for example, intertwining of the fixing plate and the sealing plate may be avoided. As the connection member is of the filament woven structure, its elastic extension and retraction may provide a wider waist length varying range.

With reference to FIGS. 1 to 10, in the naturally unfolded state of the left atrial appendage occluder, the maximum radial length of its connection member is shorter than that of the fixing plate; on one hand, one portion of the connection member may extend deep into the space encircled by the fixing plate, and on the other hand, intertwining of the connection member and the fixing plate may be avoided as much as possible in releasing and collecting processes of the left atrial appendage. In addition, as the radial length of the sealing plate is set to make the sealing plate cover the opening portion of the left atrial appendage, the maximum radial length of the connection member is also shorter than that of the sealing plate, thereby the connection member may be successfully unfolded in a left atrial appendage cavity.

According to any specific implementation embodiment of the present application, for example the left atrial appendage occluder 100 or 101 or 102, the deformability of the sealing plate 11 is greater than that of the fixing plate 12. The deformability of a certain component or structure refers to a size of a deformation amount of the component or structure under the action of an external force. In the present application, the deformability herein may be expressed by a radial length (such as diameter) variation of the component or structure under the action of a radial force. Further, the radial deformability of the sealing plate 11 of the left atrial appendage occluder is greater than that of the fixing plate 12 and/or the axial deformability of the sealing plate 11 is greater than that of the fixing plate 12. To be more specific, under the action of the same radial force, the radial length variation of the sealing plate 11 is more than that of the fixing plate 12; or under the action of the same radial force, the radial length change rate of the sealing plate 11 is more than that of the fixing plate 12; or under the action of the same axial force, the displacement of the sealing plate 11 along an axial force direction is more than that of the fixing plate along the axial force direction.

Radial length changes of the fixing plate and the sealing plate under the action of the same radial force may be respectively tested by adopting a flat plate method. For example, with reference to FIG. 11 and FIG. 12, the left atrial appendage occluder may be tested by the flat plate method.

Figure 11:
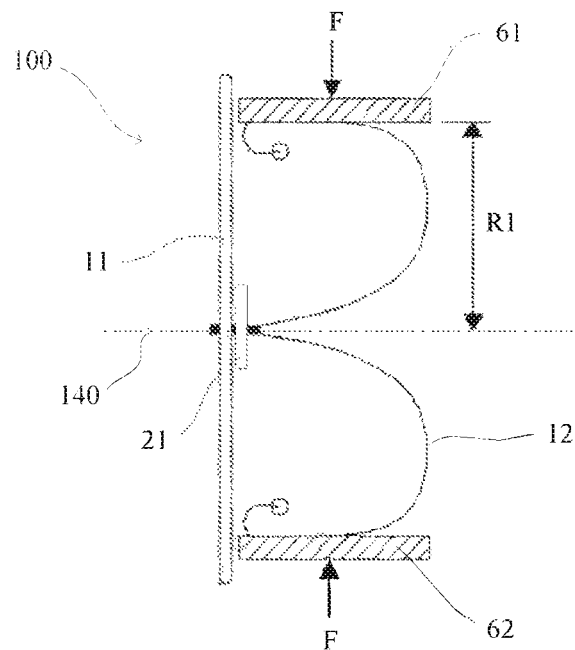
FIG. 11 is a schematic diagram of a test method of the radial deformability of a fixing plate of a left atrial appendage occluder according to one embodiment of the present application.

With reference to FIG. 11, firstly, on the premise that the sealing plate 11 maintains a freely unfolded state, two parallel flat plates 61 and 62 apply radial acting forces F to the fixing plate 12. Specifically, the parallel flat plates 61 and 62 are respectively placed on two opposite sides of a diameter of the fixing plate 12, and the radial acting forces F in the same sizes and opposite directions are respectively applied to the flat plates 61 and 62 along the diameter; the diameter of the fixing plate 12 penetrates through and is perpendicular to a central axial line 140; the two parallel flat plates 61 and 62 maintain a mutually parallel state in the whole test process, namely the flat plates are parallel to the central axial line 140 all the time in the test process; any one of the flat plates at least covers the maximum radial contour of the fixing plate 12, and preferably it covers the whole fixing plate 12 in a direction parallel to the central axial line 140. In the naturally unfolded state, if the radial lengths of portions, where the flat plates are loaded, on the fixing plate 12 are R1, the radial length variation of the fixing plate 12 under the action of the radial forces F is a radial length difference obtained before and after radial compression, and may be expressed by $\Delta R1$, so that the radial length change rate is $\Delta R1/R1$. In order to guarantee no deformation of the flat plates in a radial force applying process to uniformly apply the radial forces to all portions on the flat plates, the flat plates should have a thickness of at least 5 mm.

It should be understood that although FIG. 11 and subsequent figures all show the left atrial appendage occluder 100, the occluder is merely used as an example, and not intended to limit the present application. All the test methods or processes are applicable to any left atrial appendage occluder described based on the present application, for example the left atrial appendage occluder 101 or 102.

Figure 12:
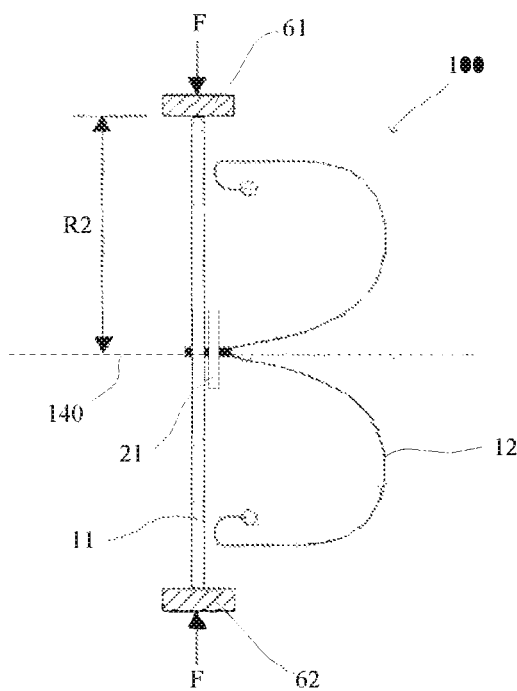
FIG. 12 is a schematic diagram of a test method of the radial deformability of a sealing plate of the left atrial appendage occluder as shown in FIG. 11.

With reference to FIG. 12, the sealing plate 11 is tested by adopting the same flat plate test method, namely adopting the same radial acting forces F including the sizes, the directions and the acting time of the acting forces F, which are the same; on the premise that the fixing plate 12 is naturally unfolded, the radial length variation $\Delta R2$ or the radial length change rate $\Delta R2/R2$ of the sealing plate 11 is tested; and at the moment, the maximum radial contour of the sealing plate 11 is located at the plate edges of the two layers of plates. Based on the above-mentioned test condition, under the action of the same radial force, the radial length variation $\Delta R2$ of the sealing plate 11 of the left atrial appendage occluder provided by the embodiment of the present application is more than that $\Delta R1$ of the fixing plate 12; or the radial length change rate $\Delta R2/R2$ of the sealing plate 11 of the left atrial appendage occluder provided by the embodiment of the present application is more than that $\Delta R1/R1$ of the fixing plate 12.

During test of the left atrial appendage occluder by adoption of the flat plate method, in order to avoid deformation of the elastic connection member 21 to adapt to radial compression of the fixing plate or the sealing plate in a flat plate radial compression process, with reference to FIG. 3, a clamping member (which is not shown in the figure, and may be any proper clamping member familiar to a person skilled in the art) may be adopted to fix one end portion of the connection member 21 in a process that the flat plates compress the fixing plate or the sealing plate. For example, when the fixing plate is compressed, the second fixed connection member 212, which is closely adjacent to the fixing plate, of the connection member 21 is clamped; and when the sealing plate is compressed, the first fixed connection member 211, which is closely adjacent to the sealing plate, of the connection member 21 is clamped.

After the left atrial appendage occluder is implanted into a human body, such a case of improper selection of an implantation position may be possibly caused, for example, the fixing plate extends too deep into the cavity of the left atrial appendage, which possibly leads to a fact that the naturally unfolded axial length of the occluder is shorter than a relative distance between the fixing plate and the sealing plate after the implantation, thus leading to mutual pulling action between the fixing plate and the sealing plate; or after being implanted, the occluder would move together with the heart, but different movement amplitudes or directions at all portions may also lead to the mutual pulling action between the fixing plate and the sealing plate. Generally, the fixing plate and the sealing plate pull each other through the connection member.

When the fixing plate is pulled by the sealing plate, and the fixing plate is fixed in the cavity of the left atrial appendage through a radial supporting force surrounding a circumferential region of the central axial line 140, the fixing plate is mainly closely fitted to the circumferential region of the cavity of the left atrial appendage to resist this pulling acting force. Therefore, axial pulling for the fixing plate would lead to radial deformation of the fixing plate; large enough pulling action would possibly lead to separation of the fixing plate from the cavity wall of the left atrial appendage, and then the left atrial appendage occluder would fall off, which causes an implantation failure. When pulled by the fixing plate, the sealing plate with a disk surface structure is connected with the connection member through the disk surface, so that the axial pulling for the sealing plate would also lead to radial deformation of the sealing plate.

Therefore, when the fixing plate and the sealing plate pull each other, one plate which easily deforms in the radial direction is pulled by the other plate, for example, under the same radial acting force, as the radial length variation of the fixing plate according to the embodiment of the present application is smaller than that of the sealing plate, or the radial length change rate of the fixing plate according to the embodiment of the present application is smaller than that of the sealing plate, in the mutual pulling process, the fixing plate would pull the sealing plate in a leading manner to make the sealing plate deform towards the fixing plate direction (or towards the distal end). Such deformation enables the sealing plate to be fitted to a left atrial wall at an opening of the left atrial appendage more closely than the naturally unfolded state, which enhances a sealing effect of the sealing plate on the opening of the left atrial appendage and avoids formation of a clearance space between the sealing plate and the left atrial wall, thereby preventing apoplexy or systematic embolization caused by blood flow flowing into the cavity of the left atrial appendage through the clearance space and a thrombus flowing into a left atrium through the clearance space. In addition, the fixing plate leads the pulling and is not easily pulled to be separated from the cavity wall of the left atrial appendage by the sealing plate, so that the occluder is better fixed in the left atrial appendage and is prevented from falling off from the left atrial appendage.

Figure 13:
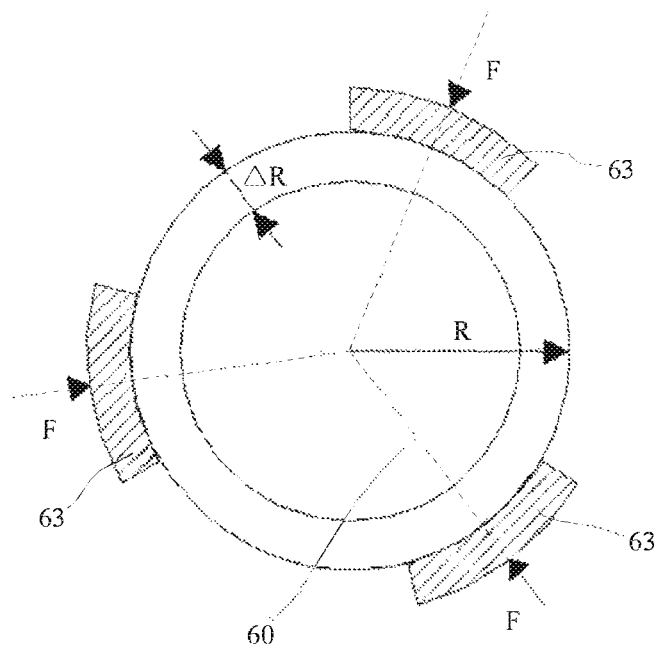
FIG. 13 is a schematic diagram of another specific test structure of the radial deformability of a sealing plate/fixing plate of a left atrial appendage occluder according to one embodiment of the present application.

The above-mentioned flat plate test method is only an example test method, but not intended to limit the present application, and a person of ordinary skill in the art can adopt any proper method for conducting the test equivalent to the flat plate test method. For example, the radial acting force is uniformly applied to the circumferential direction of a component to be tested for testing. Specifically, with reference to FIG. 13, three arc-shaped plates 63 may be uniformly disposed in the same circumferential direction of the maximum radial contour of the component to be tested (the fixing plate or the sealing plate); and during testing, the radial acting force F is simultaneously applied to the arc-shaped plates 63 along a radial direction 60 to test a variation $\Delta R$ or a change rate $\Delta R/R$ of a radial length R of the component. Similarly, in order to realize uniform application of the radial force, the arc-shaped plates should have a thickness of at least 5 mm. Furthermore, a radial supporting force tester RX550-100 of the Machine Solution Inc (MSI) Company may be adopted to test the left atrial appendage occluder.

In addition, under a condition that one portion of the component to be tested (the fixing plate or the sealing plate) is restricted, the axial deformability of the component is expressed by testing an axial displacement (along the direction of the central axial line 140) of the component under the action of the same axial force. In a first axial deformability test method, the above-mentioned restriction is equidimensional restriction, that is to say, in the restriction process, the component to be tested does not elastically deform or deforms a little, which may be ignored basically; and in addition, the axial acting force is applied to a position, where no elastic deformation occurs, on the component to be tested. For example, the same axial acting force is applied to one end portion, which is connected with the connection member, of the component to be tested to test the axial displacement of the component to express its own deformability, and the axial displacement of the component here is the axial displacement of the force application portion. The left atrial appendage occluder meets the condition that the axial displacement of the fixing plate is smaller than that of the sealing plate. During testing, the fixing plate and the sealing plate are independently tested, for example, the single fixing plate or the single sealing plate is tested at each time, so that the influence of the connection member 21 may be ignored.

Figure 14:
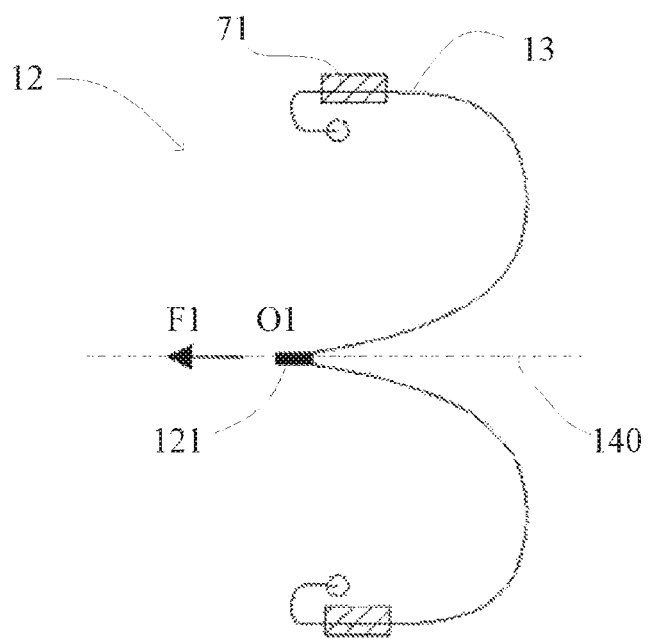
FIG. 14 is a schematic diagram of a first test method of the axial deformability of a fixing plate of a left atrial appendage occluder according to one embodiment of the present application.

With reference to FIG. 14, during testing of the fixing plate 12, an annular clamping member 71 is adopted to clamp the fixing plate 12 from the maximum radial contour of the fixing plate 12 along a circumferential direction. The annular clamping member 71 surrounds and is perpendicular to the central axial line 140. In a clamping process, the radial size of the clamped portion of the fixing plate 12 is basically maintained at the size in the naturally unfolded state, so that the elastic deformation may be ignored basically. An axial acting force F1 is applied to the end portion 121 (for example, the end portion 121 is formed by gathering one end of each supporting member 13), which is connected with the connection member, of the fixing plate 12 along the central axial line 140 and towards the direction of the sealing plate 11, and the end portion 121 does not elastically deform in the process of applying the axial acting force F1, thereby measuring the axial displacement $\Delta O1$ of a projection O1 of the end portion 121 on the central axial line 140 along with F1. The axial displacement $\Delta O1$ is adopted to express the deformation (or the deformability) of the fixing plate 12, and the clamping member 71 maintains its clamping state unchanged in the whole applying process of the axial acting force F1. It can be seen from the above that after the left atrial appendage occluder is implanted into a human body, under the condition that one portion of the fixing plate 12 is clamped, for example, under the condition that the maximum contour of the fixing plate 12 is clamped, the tested axial displacement under the action of an axial pulling force represents the axial deformability of the fixing plate pulled by the sealing plate under the restricting action of the cavity of the left atrial appendage after the occluder is implanted into the cavity of the left atrial appendage. Under the same axial pulling force, larger ΔO1 indicates easier pulling deformation of the fixing plate.

Figure 15:
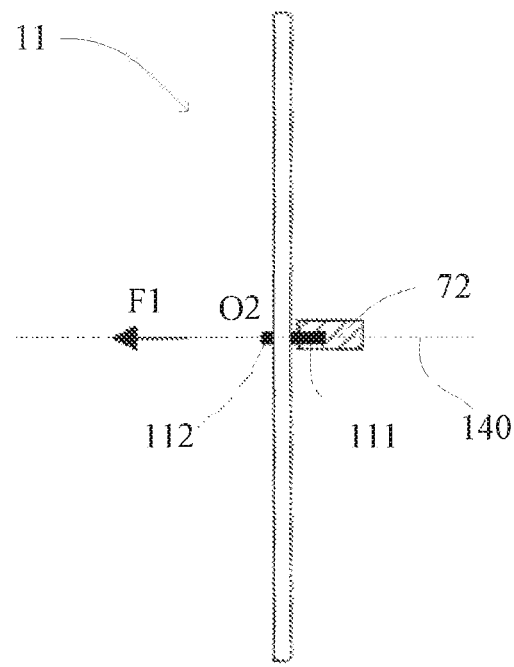
FIG. 15 is a schematic diagram of a first test method of the axial deformability of a sealing plate of the left atrial appendage occluder as shown in FIG. 14.

With reference to FIG. 15, during testing of the sealing plate 11, the clamping member 72 is adopted to directly clamp the sealing plate 11 from a distal end fixing member 111; and the axial acting force F1, which is totally the same as that in the testing process of the fixing plate 12, is applied to a proximal end fixing member (end socket) 112 of the sealing plate 11 along the central axial line 140 and towards a direction away from the clamping member 72, thereby measuring the axial displacement ΔO2 of a projection O2 of the proximal end fixing member 112 on the central axial line 140 along with F1. The axial displacement ΔO2 is adopted to express the axial deformation (or the deformability) of the sealing plate 11.

It can be seen from the above that after the left atrial appendage occluder is implanted into the human body, under the condition that one portion of the sealing plate is clamped, for example, under the condition that the distal end fixing member 111 of the sealing plate 11 is clamped, the tested axial displacement under the action of the axial pulling force F1 represents the axial deformability of the sealing plate 11 pulled by the fixing plate 12 under the restricting action of a tissue wall of the opening portion of the left atrial appendage after the occluder is implanted into the cavity of the left atrial appendage. Under the same axial pulling force, larger ΔO2 indicates easier pulling deformation of the sealing plate 11.

It is tested that under the action of the same axial force, the axial displacement ΔO1 of the fixing plate is smaller than that ΔO2 of the sealing plate. It should be understood that when the fixing plate and the sealing plate pull each other, one plate which has a larger axial displacement is pulled by the other plate, for example, under the same axial acting force, as the axial displacement of the fixing plate according to the embodiment of the present application is smaller than that of the sealing plate, in the mutual pulling process, the fixing plate would pull the sealing plate in a leading manner to make the sealing plate deform towards the fixing plate direction (or towards the distal end). Such deformation enables the sealing plate to be fitted to the left atrial wall at the opening of the left atrial appendage more closely than the naturally unfolded state, which enhances a sealing effect of the sealing plate on the opening of the left atrial appendage and avoids formation of a clearance space between the sealing plate and the left atrial wall, thereby preventing blood flow from flowing into the cavity of the left atrial appendage through the clearance space and preventing a thrombus from flowing into a left atrium through the clearance space. In addition, the fixing plate leads the pulling and is not easily pulled to be separated from the cavity wall of the left atrial appendage by the sealing plate, so that the occluder is better fixed in the left atrial appendage and is prevented from falling off from the left atrial appendage.

Figure 16:
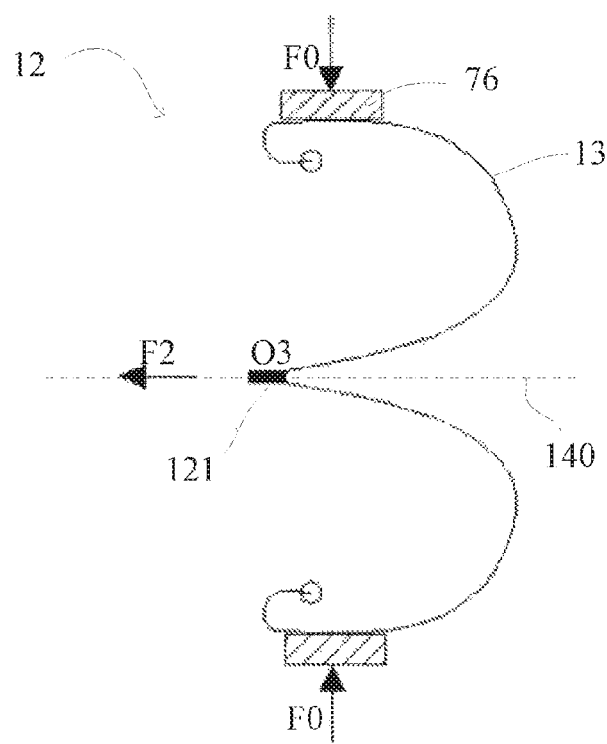
FIG. 16 is a schematic diagram of a second test method of the axial deformability of a fixing plate of a left atrial appendage occluder according to one embodiment of the present application.

A second axial deformability test method may be further adopted. With reference to FIG. 16, during testing of the fixing plate 12, an annular clamping member 76 is adopted to clamp the fixing plate 12 from the maximum radial contour of the fixing plate 12 along a circumferential direction. The annular clamping member surrounds and is perpendicular to the central axial line 140. In a clamping process, the radial size of the clamped portion of the fixing plate 12 is smaller than the size in the naturally unfolded state; the clamped portion of the fixing plat 12 is compressed in the radial direction, for example, the maximum radial length after compression is 80 percent of the maximum radial length before compression; and of course, other compression ratios may be adopted, which would not be listed one by one here. For example, a radial force F0 may be applied to the annular clamping member 76 to compress the fixing plate 12 in the radial direction. An axial acting force F2 is applied to the end portion 121, which is connected with the connection member, of the fixing plate 12 along the central axial line 140 and towards the direction of the sealing plate 11, and the end portion 121 does not elastically deform in the process of applying the axial acting force F2, thereby measuring the axial displacement 403 of a projection O3 of the end portion 121 on the central axial line 140 along with F2. The axial displacement ΔO3 is adopted to express the deformation (or the deformability) of the fixing plate 12.

It can be seen from the above that after the left atrial appendage occluder is implanted into a human body, under the condition that one portion of the fixing plate 12 is clamped, for example, under the condition that the maximum contour of the fixing plate 12 is clamped, the tested axial displacement under the action of an axial pulling force represents the deformability of the fixing plate 12 pulled by the sealing plate 11 under the restricting action of the cavity of the left atrial appendage after the occluder is implanted into the cavity of the left atrial appendage. Under the same axial pulling force, larger ΔO3 indicates easier pulling deformation of the fixing plate 12.

Figure 17:
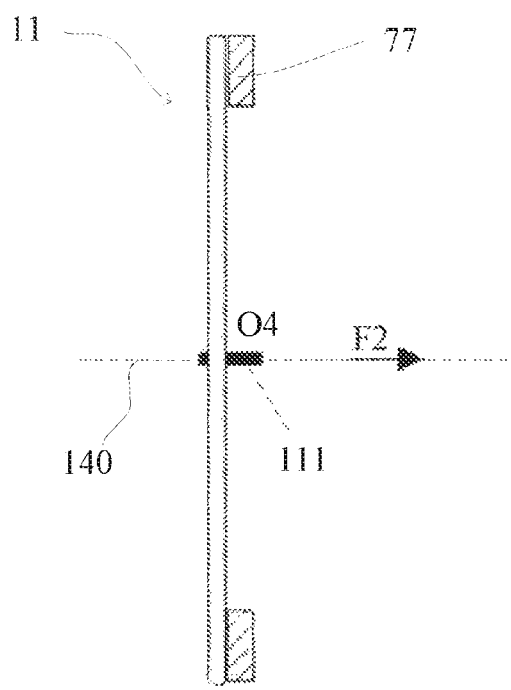
FIG. 17 is a schematic diagram of a second test method of the axial deformability of a sealing plate of the left atrial appendage occluder as shown in FIG. 16.

With reference to FIG. 17, the sealing plate 11 includes a distal end fixing member 111; and the connection member 21 is connected with the distal end fixing member 111. During independent testing of the sealing plate 11, an annular fixing member 77 is adopted to press against a disk surface, which faces to the fixing plate 12, of the sealing plate 11 from the maximum edge of the disk surface, and the axial acting force F2 is applied to the distal end fixing member 111 along the central axial line 140 and towards the direction of the fixing plate 12; and in the axial pulling process of F2, the pressed disk surface is maintained at an unchanged position along the direction of the central axial line 140 through the annular fixing member 77, thereby testing a projection displacement ΔO4 of the distal end fixing member 111 on the central axial line 140.

It can be seen from the above that after the left atrial appendage occluder is implanted into the human body, under the condition that one portion of the sealing plate is pressed by the cavity wall of the left atrium at the opening portion of the left atrial appendage, wherein at least the maximum radial edge, which faces to the fixing plate, of the sealing plate is pressed, so that in the test process of the sealing plate, under conditions that the annular fixing member presses against the maximum radial edge, which faces to the fixing plate, of the sealing plate and the maximum radial edge is kept not moving along the direction of the central axial line 140, the tested axial displacement of the sealing plate under the action of the axial pulling force represents the deformability of the sealing plate pulled by the fixing plate at the opening of the left atrial appendage after the occluder is implanted into the human body. Under the same axial pulling force, larger ΔO4 indicates easier pulling deformation of the sealing plate.

It is tested that under the action of the same axial force (F2), the axial displacement ΔO3 of the fixing plate is smaller than that ΔO4 of the sealing plate. It should be understood that when the fixing plate and the sealing plate pull each other, one plate which has a larger axial displacement is pulled by the other plate, for example, under the same axial acting force, as the axial displacement of the fixing plate according to the embodiment of the present application is smaller than that of the sealing plate, in the mutual pulling process, the fixing plate would pull the sealing plate in a leading manner to make the sealing plate deform towards the fixing plate direction (or towards the distal end). Such deformation enables the sealing plate to be fitted to the left atrial wall at the opening portion of the left atrial appendage more closely than the naturally unfolded state, which enhances a sealing effect of the sealing plate on the opening of the left atrial appendage and avoids formation of a clearance space between the sealing plate and the left atrial wall, thereby preventing blood flow from flowing into the cavity of the left atrial appendage through the clearance space and preventing a thrombus from flowing into a left atrium through the clearance space. In addition, the fixing plate leads the pulling, and is not easily pulled to be separated from the cavity wall of the left atrial appendage by the sealing plate, so that the occluder is better fixed in the left atrial appendage and is prevented from falling off from the left atrial appendage.

In the left atrial appendage occluder of the present application, the connection member is of the filament woven structure, and has high elastic extension, retraction and bending performance. It has a deformation space under a pulling force and/or a compressing force, and may provide an angle and/or length adjustment function to adapt to implantation of left atrial appendages in more shapes and sizes, and the implantation stability of the left atrial appendage occluder is improved. In addition, the mutual pulling action between the fixing plate and the sealing plate during operation and after operation may be buffered through the elastic extension, retraction and bending performance of the connection member when transmitted to the connection member, thereby reducing influence on the fixing plate and the sealing plate due to the pulling action, for example, avoiding leakage as much as possible caused by non-fitting of coverage of the sealing plate due to the fact that the sealing plate is pulled into the cavity of the left atrial appendage and avoiding injury as much as possible to the cavity wall of the left atrial appendage due to pulling of the fixing plate, which reduces a risk of hydropericardium.

All the technical features of the above embodiments may be randomly combined. In order to simplify the description, not all possible combinations of the respective technical features in the embodiments are described. However, the combinations of these technical features shall fall within the scope described in the description in case of no contradictions.

The above embodiments only express a few of implementation modes of the present application, and their descriptions are relatively specific and detailed, but shall not be regarded as limitations to the scope of the patent for the present application. It should be noted that persons of ordinary skill in the art can further make a plurality of deformations and improvements without departing from the idea of the present application, and these deformations and improvements shall all fall within the protection scope of the present application. Therefore, the scope of protection of the present application shall be based on attached claims.

The invention claimed is:

1. A left atrial appendage occluder, comprising:
a sealing plate,
a fixing plate located on one side of the sealing plate, the fixing plate comprising a plurality of supporting members cut from a metal tube, and
a connection member for connecting the sealing plate with the fixing plate, the connection member comprising a woven body having a hollow columnar structure formed by a plurality of grids created of weaving wires,
wherein each support member of the fixing plate comprises one end connected with the connection member and another end radiating and extending from the connection member;
wherein a radial deformability of the sealing plate is greater than that of the fixing plate such that under a same external force in a radial direction the sealing plate has a greater radial length change rate than the fixing plate, and/or an axial deformability of the sealing plate is greater than that of the fixing plate such that under a same external force in an axial direction the sealing plate is displaced more along the axial force direction than that of the fixing plate.

2. The left atrial appendage occluder according to claim 1, wherein under the action of same radial force, a radial length variation of the sealing plate is more than that of the fixing plate.

3. The left atrial appendage occluder according to claim 1, wherein the wires of the connection member are elastic such that the woven body is elastic.

4. The left atrial appendage occluder according to claim 1, wherein the connection member comprises a woven body having a hollow columnar structure that is disk shaped or barrel shaped in a naturally unfolded state.

5. The left atrial appendage occluder according to claim 1, wherein the peripheral surface of the connection member defines an annular recess.

6. The left atrial appendage occluder according to claim 1, wherein a recess is defined near a joint on at least one of end surfaces of the connection member connected with the sealing plate and connected with the fixing plate.

7. The left atrial appendage occluder according to claim 1, wherein, in the naturally unfolded state, the maximum radial length of the connection member is shorter than that of the fixing plate.

8. The left atrial appendage occluder according to claim 1, wherein, in the naturally unfolded state, at least one portion of the connection member extends out of a space encircled by the fixing plate.

9. The left atrial appendage occluder according to claim 1, wherein the connection member comprises a first fixed connection member, a second fixed connection member and the woven body having a hollow columnar structure formed by a plurality of grids of weaving wires; the first end of the woven body is collected and fixed by the first fixed connection member; and the second end of the woven body is collected and fixed through the second fixed connection member.

10. The left atrial appendage occluder according to claim 1, wherein the sealing plate comprises a filament woven structure; one end of the sealing plate is connected with one side of the connection member; each supporting member of the fixing plate radiates and extends from the other side of the connection member; and the supporting members cooperatively form an umbrella-shaped structure.

11. The left atrial appendage occluder according to claim 1, wherein the sealing plate formed of a woven body formed by weaving wires.

12. The left atrial appendage occluder according to claim 11, wherein in the naturally unfolded state without application of an external force, the maximum radial length of the connection member is shorter than that of the fixing plate and that of the sealing plate.

13. The left atrial appendage occluder of according to claim 1, wherein the fixing plate further comprises film bodies forming an outer surface of the fixing plate and fixed on the plurality of supporting members.

* * * * *